US00PP10829P

United States Patent [19]

Fleming

[11] Patent Number: Plant 10,829

[45] Date of Patent: Mar. 16, 1999

[54] KALANCHOE PLANT NAMED 'RIGHT CHOICE'

[75] Inventor: Margaret Marne Fleming, Soquel, Calif.

[73] Assignee: The Plant Co., Half Moon Bay, Calif.

[21] Appl. No.: 938,576

[22] Filed: Sep. 26, 1997

[51] Int. Cl.[6] ..... A01H 5/00

[52] U.S. Cl. ..... Plt./87.15

[58] Field of Search ..... Plt./87.15

[56] References Cited

U.S. PATENT DOCUMENTS

P.P. 9,674 10/1996 Drewlow ..... Plt./87.15

*Primary Examiner*—Howard J. Locker

*Attorney, Agent, or Firm*—C. A. Whealy

[57] ABSTRACT

A distinct cultivar of Kalanchoe plant named 'Right Choice', characterized by its uniform and stable soft salmon pink flower color; upright plant habit; full plants, freely branching habit with shoots forming at every node; uniform plant habit and inflorescence display; small to medium dark green glossy leaves; proportional leaf size to plant size; numerous flowers per plant; medium to large flowers; resistance to Botrytis, Rhizoctonia and Fusarium; and excellent postproduction longevity.

1 Drawing Sheet

The present invention relates to a new and distinct cultivar of Kalanchoe plant, botanically known as *Kalanchoe blossfeldiana* Adans., and hereinafter referred to by the cultivar name 'Right Choice'.

The new cultivar is a product of a planned breeding program conducted by the inventor in Soquel and Half Moon Bay, Calif. The objective of the breeding program was to create new Kalanchoe cultivars having a uniform and compact plant habit; freely branching habit; attractive flower and foliage colors; short response time; resistance to diseases and insects; and good postproduction longevity.

The new cultivar originated from a cross made by the inventor of the proprietary *Kalanchoe blossfeldiana* Adans. selection code number 708-011 as the male, or pollen, parent with the proprietary *Kalanchoe blossfeldiana* Adans. selection code number 619-002 as the female, or seed, parent.

Compared to the male parent, plants of the new Kalanchoe flower one week later and have a different flower color. Compared to the female parent, plants of the new Kalanchoe flower one week earlier and have a different flower color.

The cultivar 'Right Choice' was discovered and selected by the inventor in July, 1993, as a flowering plant within the progeny of the stated cross in a controlled environment in Soquel, Calif.

Asexual reproduction of the new cultivar by terminal and node cuttings taken at Soquel and Half Moon Bay, Calif., has shown that the unique features of this new Kalanchoe are stable and reproduced true to type in successive generations.

The cultivar 'Right Choice' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Right Choice'. These characteristics in combination distinguish 'Right Choice' as a new and distinct cultivar:

1. Uniform and stable soft salmon pink flower color.
2. Upright plant habit.
3. Full plants, freely branching habit with shoots forming at every node. Plants do not require pinching.
4. Uniform plant habit and inflorescence display.
5. Small to medium dark green glossy leaves.
6. Proportional leaf size to plant size.

7. Numerous flowers per plant.
8. Medium to large flowers.
9. Resistant to Botrytis, Rhizoctonia and Fusarium.
10. Not attractive to aphids.
11. Excellent postproduction longevity.

The new Kalanchoe is most similar in flower color to the commercial cultivar, 'Eternity' (disclosed in U.S. Plant Pat. No. 5,253). However, in side-by-side comparisons in Soquel and Half Moon Bay, Calif., plants of the new Kalanchoe were more freely branching; had smaller, less succulent and more durable foliage; flowered about two weeks earlier; and more uniform flower color. Flower color of plants of the cultivar 'Eternity' will vary from deep salmon red under winter conditions to tan under summer conditions whereas plants of the new Kalanchoe maintain their soft salmon flower color year round.

BRIEF DESCRIPTION OF THE PHOTOGRAPH

The accompanying colored photograph illustrates the overall appearance of the new cultivar, showing the colors as true as it is reasonably possible to obtain in colored reproduction of this type. The photograph comprises a top perspective view of a typical potted plant of 'Right Choice' taken in Soquel, Calif. Flower color in the photograph may appear different from the actual color due to light reflectance.

DETAILED BOTANICAL DESCRIPTION

In the following description, color references are made to The Royal Horticultural Society Colour Chart except where general terms of ordinary dictionary significance are used. Measurements and numerical values represent typical plants in 10.5-cm containers that were grown during the spring in Northern California. Plants were grown under cultural and environmental conditions that approximated commercial practice in a plastic-covered greenhouse with day temperatures ranging from 16 to 38° C. and night temperatures ranging from 4.5 to 13° C. Plants were exposed to five weeks of long day/short nights followed by six weeks of short day/long night photoperiodic treatments.

Botanical classification: *Kalanchoe blossfeldiana* Adans. cultivar 'Right Choice'.

Parentage:

*Male or pollen parent.*—Proprietary *Kalanchoe blossfeldiana* Adans. selection code number 708-011.

*Female or seed parent.*—Proprietary *Kalanchoe blossfeldiana* Adans. selection code number 619-002.

Propagation:

*Type cutting.*—Terminal cuttings.

*Time to initiate roots.*—10 to 12 days at 21° C. soil temperature.

*Time to develop roots.*—About 20 days at 18° C. soil temperature.

*Rooting habit.*—Numerous, fine, fibrous, and well-branched.

Plant description:

*Form.*—Upright and uniform. Plant shape is an inverted triangle with a rounded apex.

*Branching habit.*—Freely branching, generally shoots formed at every node. Plants do not require pinching.

*Plant height at flowering.*—About 19 cm from soil level to top of plant, about 17.5 cm in diameter, appropriate for 10.5 to 15cm containers.

*Vigor.*—Moderately vigorous and moderate growth rate.

*Production time.*—Three to 6 weeks of long day/short night conditions followed by about 6 weeks of short day/long night conditions are required to initiate and develop flowers. Plants are in flower 4 to 5 weeks later. Depending on environmental conditions, a total of 13 to 17 weeks is required.

*Foliage description.*—Leaves simple, opposite, generally symmetrical. Length: About 7.5 cm. Width: About 5.5 cm. Shape: Ovate. Apex: Acute. Base: Obtuse. Margin: Crenate. Texture: Leathery, glabrous, glossy, coriaceous and succulent. Petiole length: About 1.5 cm. Color: Young foliage upper surface: Darker than 147A. Young foliage lower surface: 147A. Mature foliage upper surface: Darker than 147A. Mature foliage lower surface: Lighter than 147A. Petiole: 146A. Stem color: 146A.

Flower description:

*Flower type and habit.*—Single flowers arranged in compound dichasial cymes on strong peduncles. Freely flowering and very floriferous with new buds continuing to develop. Uniform inflorescence display.

*Natural flowering season.*—Plants flower under natural daylengths during the autumn and winter. Flower initiation and development can be induced under short day/long night conditions. After induction, opening of new buds continuous. Flowers persistent.

*Inflorescences borne.*—Above foliage, arising from leaf axils. Inflorescence of each shoot is formed by dichotomous branching.

*Time to flower.*—Under optimal environmental and cultural conditions, plants of the cultivar 'Right Choice' will start flowering after 10 or 11 weeks after start of controlled photoperiods (short day/long night conditions). First flower open is the terminal flower at the main axis and is followed by the opening of the terminal flowers of the side branches of the inflorescence.

*Flower diameter.*—About 1.4 cm.

*Flower depth* (*height*).—About 1.3 cm.

*Quantity.*—More than 175 flowers per plant.

*Flower buds.*—Length: About 1.3 cm. Width: About 4 mm. Shape: Oblong becoming tubular/ovoid with development. Rate of opening: Rapid. Color: Initially green, 144A, becoming salmon green just before opening, then light salmon, 39B.

*Petals.*—Quantity: Four. Length: About 6 mm. Width: About 5 mm. Shape: Ovate. Apex: Acuminate to cuspidate. Margin: Entire. Texture: Glabrous, smooth and satiny. Aspect: Mostly flat. Color: When opening, upper surface: 39A. When opening, lower surface: 39C with red streaks. Mature, upper surface: 39B. Mature, lower surface: 39C with red streaks. Throat: Light green, 144B, translucent. Tube: Light green, 144A, translucent.

*Sepals.*—Quantity: Four. Length: About 5 mm. Width at base: About 2 mm. Shape: Linear. Apex: Pointed. Margin: Entire. Texture: Glabrous. Aspect: Upright. Color: 145B.

*Peduncle.*—Aspect: Strong, erect, rigid, and upright. Length: About 7 mm. Texture: Glabrous. Color: 146B.

*Reproductive organs.*—Stamens: Stamen number: Eight. Anther size: About 0.5 mm. Anther shape: Flat, oblong. Pollen color: Yellow, close to 12A/12B. Amount of pollen: Moderate. Pistils: Pistil number: Four. Stigma shape: Flat. Stigma color: Light yellow, close to 9D.. Style length: About 1 cm. Style color: 144A. Ovary number: Four-celled.

Disease resistance: Plants of the new Kalanchoe have been observed to be resistant to Botrytis, Rhizoctonia and Fusarium.

Insect resistance: Plants of the new Kalanchoe are not attractive to aphids.

Seed production: Seed production has not been observed.

It is claimed:

1. A new and distinct cultivar of Kalanchoe plant named 'Right Choice', as illustrated and described.

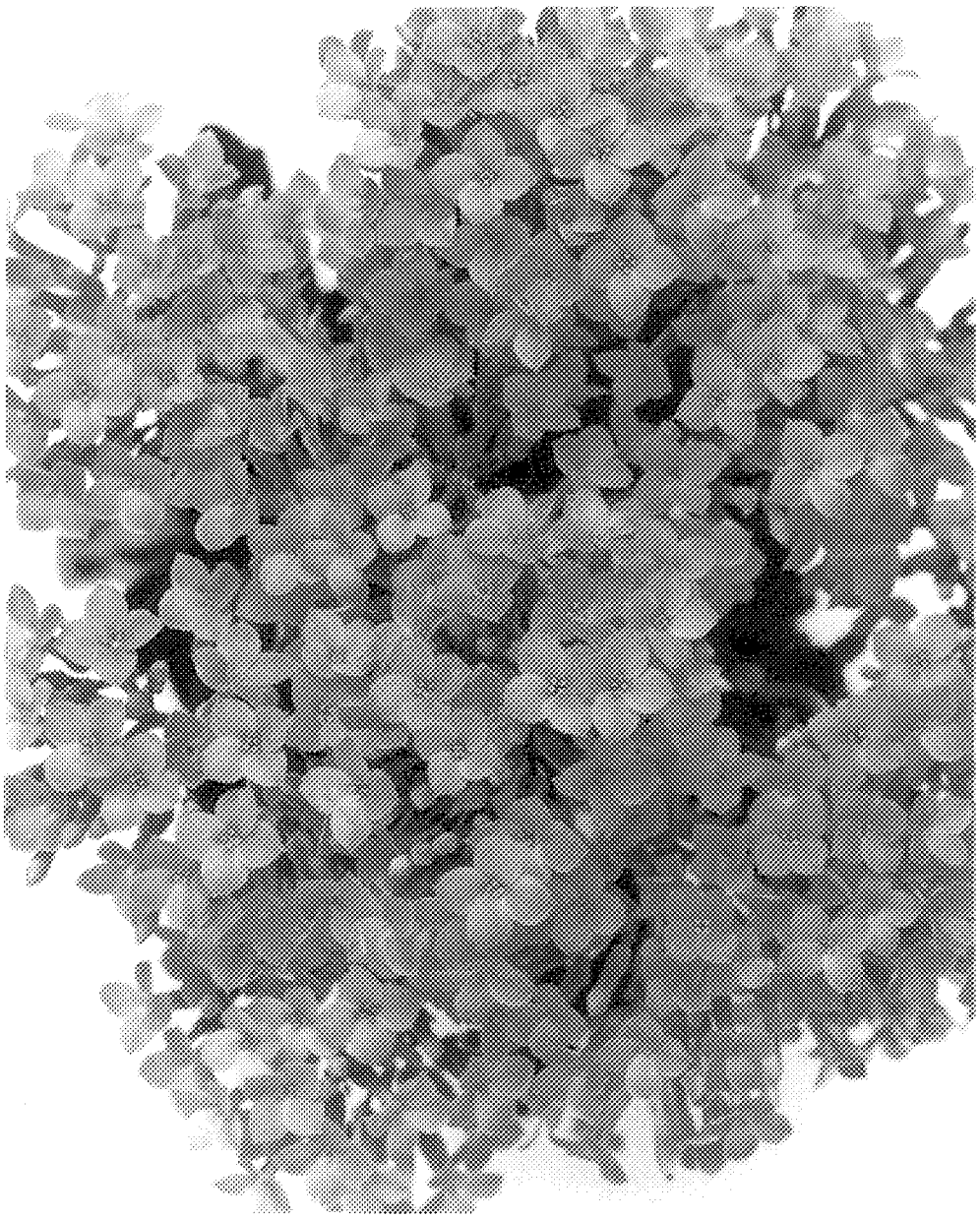

* * * * *